United States Patent [19]
Choi

[11] Patent Number: 6,069,010
[45] Date of Patent: *May 30, 2000

[54] HIGH THROUGHPUT GENE INACTIVATION WITH LARGE SCALE GENE TARGETING

[75] Inventor: Theodore Kyu Choi, La Jolla, Calif.

[73] Assignee: AxyS Pharmaceuticals, Inc., South San Francisco, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/711,218

[22] Filed: Sep. 9, 1996

Related U.S. Application Data

[60] Provisional application No. 60/003,507, Sep. 11, 1995.

[51] Int. Cl.$^7$ .......................... C12N 15/00; C12N 15/63; C12N 15/09; C12N 5/00
[52] U.S. Cl. ...................... 435/477; 435/471; 435/354; 435/325; 435/243; 435/252.33; 435/6; 800/18; 800/21; 800/22; 800/25
[58] Field of Search ................................. 514/44; 800/2, 800/18, 21, 22, 25; 435/252.3, 254.2, 243, 325, 172.3, 477, 471, 354, 252.33, 6

[56] References Cited

U.S. PATENT DOCUMENTS

| | | | |
|---|---|---|---|
| 4,963,487 | 10/1990 | Schimmel | 435/172.1 |
| 5,427,910 | 6/1995 | Kamentsky et al. | . |
| 5,695,995 | 12/1997 | Weintraub et al. | 435/325 |
| 5,733,760 | 3/1998 | Lu et al. | 435/172.3 |

OTHER PUBLICATIONS

Nakayama et al. (FEMS Microbiology Letters 128 (3). May 15, 1995.
Nehls et al. (Biotechniques 17 (4). 1994. 770–775.
Bradley et al. Bio/Technology.10:534–539, May 1992.
Degryse et al. Yeast. 11:629–640, Jun. 1995.
Mansour et al. Nature. 336: 348–352, 1988.
Capecchi (1989) "Altering the Genome by Homologous Recombination" *Science* 244:1288–1292.
Capecchi (1989) "The New Mouse Genetics: Altering the Genome by Gene Targeting" *Trends Genet.* 5:70–76.
Kuehn (1987) "A Potential Animal Model for Lesch–Nyhan Syndrome Through Introduction of HPRT Mutations Into Mice" *Nature* 326:295–298.
te Riele et al. (1992) "Highly Efficient Gene Targeting in Embryonic Stem Cells Through Homologous Recombination with Isogenic DNA Constructs" *P.N.A.S.* 89:5128–5132.
Jakobovits et al. (1993) "Germ–line Transmission and Expression of a Human–derived Yeast Artificial Chromosome" *Nature* 362:255–258.
Schedl et al. (1993) "A Yeast Artificial Chromosome Covering the Tyrosinase Gene Confers Copy Number–dependent Expression in Transgenic Mice" *Nature* 362:258–261.
Strauss et al. (1993) "Germ Line Transmission of a Yeast Artificial Chromosome Spanning the Murine $\alpha_1(1)$ Collagen Locus" *Science* 259:1904–1907.
Lamb et al. (1993) "Introduction and Expression of the 400 Kilobase Precursor Amyloid Protein Gene in Transgenic Mice" *Nat. Genet.* 5:22–30.
Pearson and Choi (1993) "Expression of the Human δ–amyloid Precursor Protein Gene From a Yeast Artificial Chromosome in Transgenic Mice" *P.N.A.S.* 90:10578–10582.
O'Conner et al. (1989) "Construction of Large DNA Segments in *Escherichia coli*" *Science* 244:1307–1312.
Pierce et al. (1992) "A Positive Selection Vector for Cloning High Molecular Weight DNA by the Bacteriophage P1 System: Improved Cloning Efficacy" *P.N.A.S.* 89:2056–2060.
Shizuya et al. (1992) "Cloning and Stable Maintenance of 300–kilobase–pair Fragments of Human DNA in *Escherichia coli* using an F–factor–based Vector" *P.N.A.S.* 89:8794–8797.
Hollifield et al. (1987) "Efficient RecABC–dependent, Homologous Recombination Between Coliphage Lambda and Plasmids Requires a Phage ninR Region Gene" *Mol. Gen. Genet.* 210:248–255.
King and Richardson (1986) "Role of Homology and Pathway Specificity for Recombination Between Plasmids and Bacteriophage _" *Mol. Gen. Genet.* 204:141–147.
Watt et al. (1985) "Homology Requirements for Recombination in *Escherichia coli*" *P.N.A.S.* 82:4768–4772.
Trask (1991) "DNA Sequence Localization in Metaphase and Interphase Cells by Fluorescence in Situ Hybridization" *Methods of Cell. Biol.* 35:3–35.

*Primary Examiner*—Jasemine C. Chambers
*Assistant Examiner*—Jill D. Martin
*Attorney, Agent, or Firm*—Pamela J. Sherwood; Paula A. Borden; Bozicevic, Field & Francis, LLP

[57] ABSTRACT

The present invention provides a vector system that is useful for the generation of mutations in a recombination-based construction method. The invention further includes the incorporation of mutations generated by the method of the present invention into mouse embryonic stem cells and transgenic mice.

14 Claims, 3 Drawing Sheets acgtgtcgatcgatcgtaggctagccactcgataac
gatcgatcgatcggGCTAGACAGATG
CGCTTAGCGGATAGTTTCGATG
GCgtaggctaggcgagtaaatctgatcggt
ctagagatcgatcgatacgatcgacgattggg
ctagactagagatcgatcgatcgatcgactg
attgggctactagagatcgatacgatcg
acgattgggctagagatcgatcgatacgatc

*Derive recombination sequence from EST or cDNA*

FIG. 1A

*Hybridize and identify BAC clone on filter (V1)*

FIG. 1B

*Insert recombination sequence in V2*

FIG. 1C

*Recombination of V1 and V2*

FIG. 1D

*Linearize recombinant vector at cleavage site*

FIG. 1E

*Introduce vector into embryonic stem cells*

FIG. 1F

HIGH THROUGHPUT GENE INACTIVATION WITH LARGE SCALE GENE TARGETING

This application claims priority of U.S. provisional patent application no. 60/003,507, filed Sep. 11, 1995.

INTRODUCTION

1. Technical Field

The field of this invention is recombination based methods for the generation of vectors and transgenic animals having a specific DNA sequence disruption.

2. Background

Recently, a massive research effort has been directed toward characterization of the human genome. It is hoped that through biochemical and functional characterization of human genes, pharmaceutical products can be developed for treatment of complex human disorders. Through the work of the Human Genome Project and related research efforts, much progress has been made toward developing new tools and strategies for mapping and cloning genes based on their position in the genome, i.e. positional cloning.

Positional cloning has proven to be a successful approach to finding disease genes, but it can be very labor intensive. The effort required to map and clone disease genes increases significantly as the search moves from centimorgans (genetic mapping) to nucleotides (physical mapping). As was demonstrated with cystic fibrosis and Huntington's disease, substantial effort is needed to progress from a critical region of a few megabase pairs (Mbp) to identifying the disease gene.

Several approaches, such as exon trapping (Buckler et al. (1991) P.N.A.S. 88:4005–4009) and direct selection (Morgan et al. (1992) N.A.R. 20:5173–5179) have been developed to find candidate genes in large genomic regions. These are then sequenced and used to isolate putative mutant cDNAs from patient cells. Often, the cell types expressing the candidate gene are unknown or inaccessible, and exons must be isolated and sequenced from genomic DNA to find sequence differences. When putative mutations are found, heterogeneity in the mutant population is needed to distinguish between linked polymorphism and causative mutation.

One of the strengths of positional cloning is that no assumptions are made about the physiological role of the disease gene. Identification is based on the genetic segregation of a particular sequence with a phenotypic trait. However, after a disease gene is identified, analysis of the biological role of the positionally cloned gene in disease progression may be difficult. To move forward with drug development, the role of genes in the onset and advancement of disease must be determined. Small animal models have been proven to be a useful tool in understanding disease processes at an organismal level.

Transgenic mice are experimentally accessible animal models of disease, however, the time and labor requirements for conventional transgenic technologies have hampered their usefulness. Although the "gene knockout" mouse is the standard for a loss-of-function model, inactivating more than a few candidate genes is currently a daunting proposition. Rapidly increasing resources such as mouse and human expressed sequence tag (EST) databases greatly simplify identifying candidate genes of interest, but these expanding resources require more efficient methods for gene targeting in the mouse.

Current methods for gene targeting in mouse embryonic stem (ES) cells are not easily scalable, that is, are not amenable to generating large numbers of gene targeting events. Procedures such as mapping intron/exon boundaries, building restriction maps, building targeting vectors, and establishing a polymerase chain reaction (PCR) or Southern-based screening assay for homologous recombination are labor intensive, and the results are unique to the specific genomic fragment. Current cell culture procedures are also inefficient. After electroporation of the targeting construct, several hundred primary ES clones are picked and expanded to provide sufficient DNA for Southern analysis. A high level of cell culture support is necessary to maintain and process these clones. PCR based screening methods are less demanding of resources, but limit the design of targeting constructs, particularly in the length of flanking homologies, and are not particularly robust. These cellular and molecular steps typically consume 100 days or more per locus, and limit the rate at which genes can be targeted in ES cells.

In the ten years since gene targeting in ES cells was first reported, the number of genes inactivated by homologous recombination total less than a few hundred loci. Methods for high-throughput generation of transgenic animals are therefore of interest.

Relevant Literature

Methods of altering mammalian genomes through homologous recombination are described in Capecchi (1989) *Science* 244:1288–1292; Capecchi (1989) *Trends Genet.* 5:70–76; and Kuehn (1987) *Nature* 326:295–298. te Riele et al. (1992) *P.N.A.S.* 89:5128–5132 disclose highly efficient gene targeting with isogenic DNA constructs. A number of articles have been published that describe the use of YACs in the generation of transgenic mice, including Jakobovits et al. (1993) *Nature* 362:255–8; Schedl et al. (1993) *Nature* 362:258–61; Strauss et al. (1993) *Science* 259:1904–7; Lamb et al. (1993) *Nat. Genet.* 5:22–30; and Pearson and Choi (1993) *P.N.A.S.* 90:10578–82.

The construction and stable maintenance of bacterial vectors containing large segments of mammalian DNA is described in O'Conner et al. (1989) *Science* 244:1307–1312; Pierce et al. (1992) *P.N.A.S.* 89:2056–2060 (1992); and Shizuya et al. (1992) *P.N.A.S.* 89:8794–8797.

The requirements for homologous recombination between plasmids and bacteriophage lambda are discussed in Hollifield et al. (1987) *Mol. Gen. Genet.* 210:248–255; King and Richardson (1986) *Mol. Gen. Genet.* 204:141–147; and Watt et al. (1985) *P.N.A.S.* 82:4768–4772.

The use of fluorescence in situ hybridization to localize DNA sequences is described in Trask (1991) *Methods Cell. Biol.* 35:3–35 and U.S. Pat. No. 5,427,910 issued Jun. 27, 1995 (Kamentsky and Kamentsky).

SUMMARY OF THE INVENTION

Vectors and methods are provided to increase the efficiency of gene targeting procedures, and generation of transgenic mice. The subject methods utilize a two vector system. The first vector (V1) comprises a sequence of interest from a mammalian genome. A single genomic clone may be used, or a library that encompasses all or part of the mammalian genome. The second vector (V2) comprises a recombination sequence, which is similar or identical in sequence to a region of the V1 genomic sequence. Preferably the recombination sequence is a portion of a coding region of a gene. The V1 and V2 vectors are chosen to have compatible origins of replication in a bacterial cell. Upon introduction of both vectors into a single bacterial cell, recombination occurs, inserting V2 into V1 at the recombination sequence to create a single "knock-out" vector.

To generate transgenic animals, the knock-out vector is introduced into embryonic stem (ES) cells in accordance with conventional methods. An improvement in screening for targeted cells is provided, where fluorescence in situ hybridization is used to differentiate between targeted, homologous recombination and random integration of the vector into the ES cell genome. The targeted ES cells comprise a disrupted genomic sequence at one loci. The ES cells are then used to generate transgenic animals having a heterozygous or homozygous gene knock-out.

BRIEF DESCRIPTION OF THE DRAWINGS

FIGS. 1A to 1F schematically illustrates the construction of a gene disruption in a selected DNA sequence and preparation for introduction of the gene disruption into mouse embryonic stem (ES) cells.

DESCRIPTION OF THE SPECIFIC EMBODIMENTS

Figure 2A:
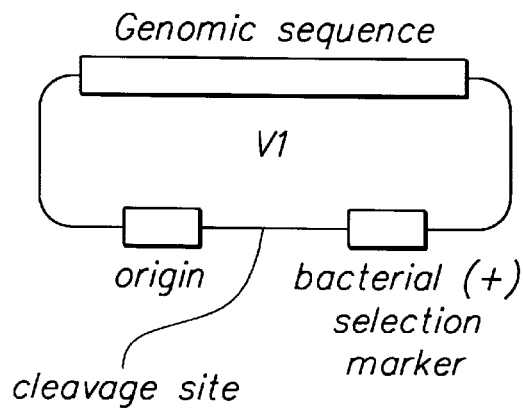
FIGS. 2A through 2C schematically illustrate the vectors used int he subject gene disruption.

Vectors and methods are provided to increase the efficiency of gene targeting procedures, and generation of transgenic mice. A two vector system that takes advantage of highly efficient bacterial homologous recombination pathways is used to generate recombinant vectors having a specific disruption in a genomic sequence. The disrupted, knock-out vector is then used to generate transgenic mice having a loss of function at the disrupted locus. The first vector (V1) comprises a mammalian genomic sequence. The second vector (V2) comprises a recombination sequence, which is similar or identical to a region of the V1 genomic sequence. V2 is introduced into a bacterial cell carrying V1 under conditions permissive for homologous recombination, whereby V2 is inserted into V1 at the recombination sequence, knocking-out the locus at the site of insertion.

To generate transgenic animals, the knock-out vector is introduced into embryonic stem (ES) cells in accordance with conventional methods. An improvement in screening for targeted cells is provided, where fluorescence in situ hybridization is used to differentiate between targeted, homologous recombination and random integration of the vector into the ES cell genome. The targeted ES cells comprise a disrupted genomic sequence at one loci. The ES cells are then used to generate transgenic animals having a heterozygous gene knock-out, which animals may be bred to generate homozygous knock-outs.

The subject methods allow high level production of animal models for human genetic disorders. Such animal models serve as an experimentally accessible platforms for identifying genes, and for dissecting biological mechanisms underlying disease. Such a loss-of-function approach to analyzing gene function is particularly useful when no appropriate mouse model exists for the selected genetic locus. The subject invention improves the efficiency of ES cell gene targeting, shifting almost all of the time and effort in gene targeting to the actual production of mice.

The use of homologous recombination between the genomic DNA on V1 and a specified sequence on V2 allows the generation of targeted knock-outs with essentially no molecular characterization of the intron/exon structure of the gene. The location of the insertion is specified by sequence, rather than by the availability of convenient restriction sites, which permits targeting of the insertion to particular motifs or sequences of interest with great precision. The method of the present invention is amenable to construction of targeting constructs assembled in parallel.

The V1 vector comprises a mammalian genomic sequence of interest, a cleavage site for an endonuclease that cuts once in the vector backbone, and several functional regions necessary for episomal maintenance and selection in a bacterial host. The genomic DNA may be obtained from any mammalian species, e.g. bovine, feline, canine, ovine, primate, murine, lagomorph, rodent, etc. Of particular interest are human and mouse genomic clones. In a preferred embodiment, the ES cells and the genomic DNA will be from the same strain of animal, in order to maximize targeting efficiency. The genomic sequence will usually be at least about 25 kb in length, more usually at least about 50 kb, and preferably at least about 100 kb. In most cases the inserted genomic DNA will be less than about 300 kb.

Suitable libraries of mouse or human genomic DNA cloned into a bacterial artificial chromosome (BAC) are commercially available, for example from the Whitehead Institute for Biomedical Research, 9 Cambridge Center, Cambridge, Mass. 02142. PAC or P1 libraries are available from Genome Systems, 8620 Pennell Drive, St. Louis, Mo. 63114. Alternatively, libraries may be created according to conventional methods (for example, see O'Conner et al.; Pierce et al.; and Shizuya et al., supra.) It is desirable to maintain such libraries in host cells, rather than subject the BACs to multiple transformation events.

The V1 vector has an origin of replication that is functional in a bacterial cell, and that maintains the vector as a single copy in the cell. The origin will chosen from those known in the art to have these characteristics in the selected bacterial host cell. Suitable host cell species include *E. coli* and other gram negative rods, such as Pseudomonas, Erwinia, Shigella, Salmonella, Proteus, Klebsiella, Enterobacter and Yersinia. Other species of interest include *B. subtilis*, Streptomyces, etc. The genetics and growth requirements of *E. coli* are well known, and in most cases it will be the preferred host. For use with an *E. coli* host, the F factor origin of replication is exemplary, although other origins, e.g. P1, etc. may also find use.

A selectable marker active in bacterial cells is also present on V1. Typically such markers encode resistance to an antibiotic or other drug. When bacteria transformed with the vector are grown in the presence of the drug, only those cells comprising the vector are able to survive. Many selectable markers are well-characterized and known in the art, e.g. resistance to ampicillin (β-lactamase); chloramphenicol (chloramphenicol acetyl transferase); kanamycin, streptomycin; tetracycline; etc.

In addition to the functional regions required for selection and maintenance, there are features necessary for the function of the final recombinant, knock-out vector. One such feature is a site for cleavage by an endonuclease that is unique in the backbone of the knock-out vector, where backbone is intended to refer to the vector sequences apart from the inserted mammalian genomic DNA. The vector is linearized when cut at that site. Preferably the restriction endonuclease will be one that cuts mammalian DNA infrequently, e.g. Not I, Sfi I, I-Ppo I, I-Sce I, etc. The cleavage site may be present in one of the vector backbones, or may be introduced into V1 through various means known in the art. In order to minimize in vitro manipulation of genomic clones, it is preferable to introduce the cleavage site, when necessary, through bacterial recombination. For example, a fragment of DNA comprising the recognition sequence for the enzyme, and flanked on both sides by from about 50 to 5000 nt of DNA, identical in sequence to the V1 vector backbone, is introduced into a bacterial cell carrying the genomic clone(s) under conditions permissive for homologous recombination.

Figure 2B:
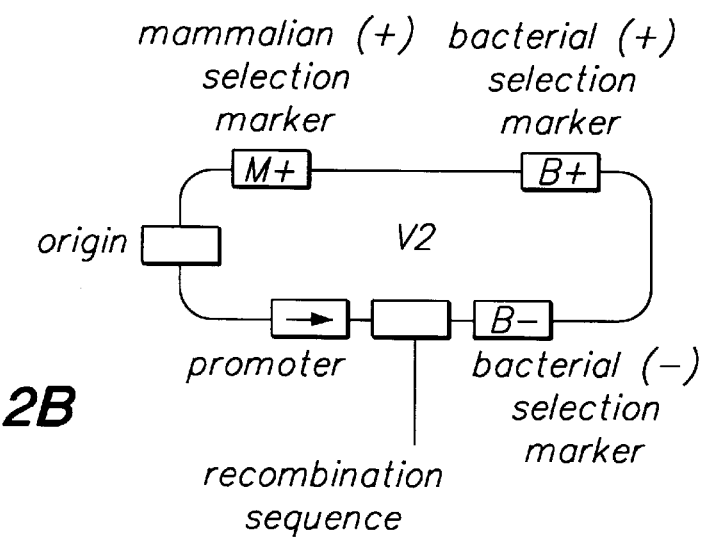
Figure 2C:
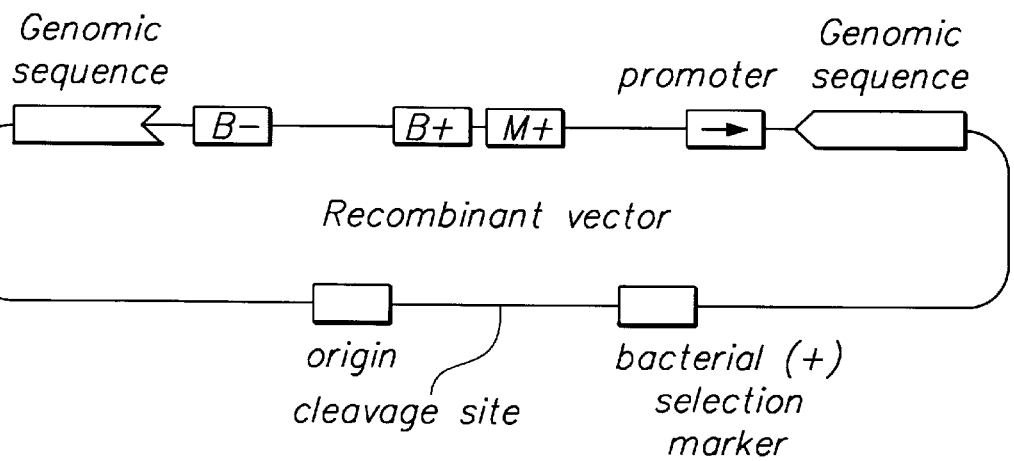
Figure 3A:
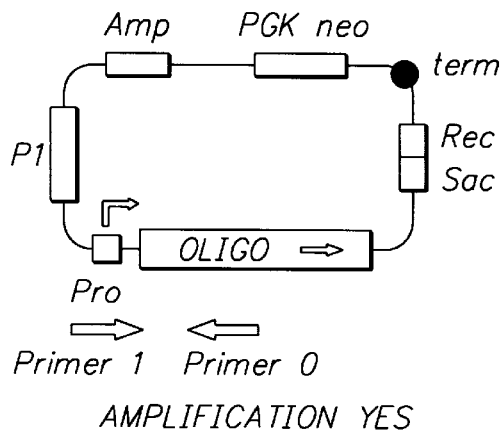
FIGS. 3A to 3D show the relationship between amplification primers and possible gene orientations.
Figure 3B:
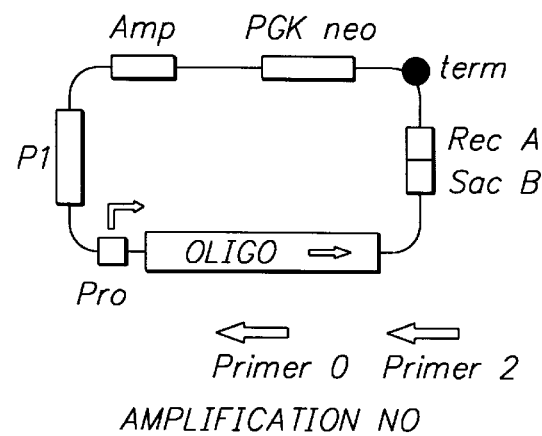
Figure 3C:
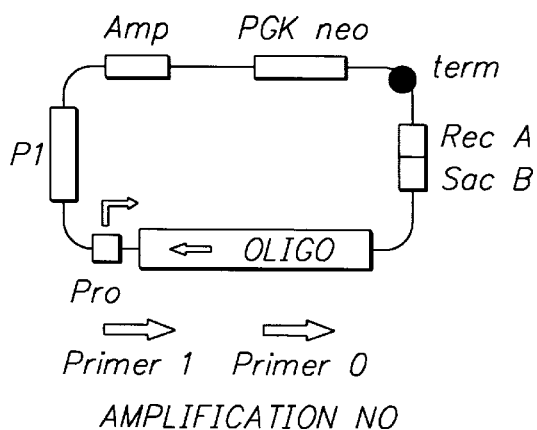
Figure 3D:
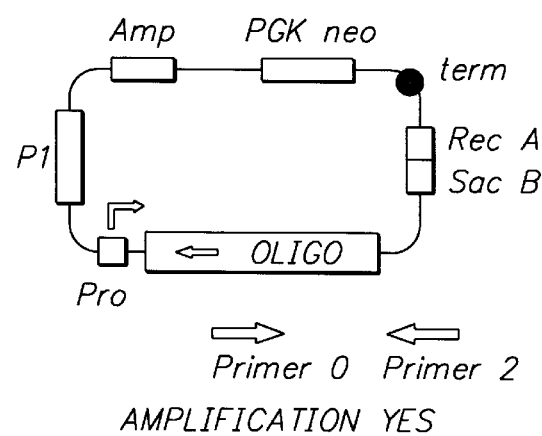

Although not necessary for the practice of the invention, it may be desirable to have one or more negative selection markers active in mammalian cells present on V1. The negative selection marker(s) flank the genomic DNA in the vector before and after linearization at the unique cleavage site previously described. The arrangement of elements is shown in FIGS. 2B and 2C. When the final knock-out vector is introduced into ES cells, it can integrate into the mammalian genome by random or by homologous recombination, where homologous integration is the desired event. The negative selection marker(s) are cleaved off in the event of a homologous recombination event between the knockout vector and the endogenous genome sequence. Loss of the negative selection marker(s) permit the mammalian cell to survive the appropriate selection. If the vector integrates non-homologously into the mammalian genome, then the negative selection cassettes are typically not lost, and selection against the negative selection cassette kills the mammalian cell. This process enriches for mammalian cells harboring homologous recombination events, as described by Capecchi et al. (1989A), supra.

One negative selection marker on one side of the single cut cleavage site is sufficient, although two, one each on either side may be preferable. The markers need not be identical. Two markers are typically situated in a head-to-head orientation, such that if there were homologous recombination in the bacterial cell between them, it would not result in the deletion of one of the markers and the cleavage site.

The negative selection marker typically comprises a promoter that is functional in mammalian cells fused to a gene that encodes a product that is toxic or an enzyme that catalyzes formation of a toxic product. Examples of suitable markers include HSV-TK used in combination with acyclovir or gancyclovir; HPRT used with 6-thioguanine; GPT used with 6-thioguanine; diphtheria toxin; ricin toxin; cytosine deaminase used with 5-fluorocytosine; and the like.

The second vector, V2, comprises a recombination sequence which is substantially identical to a portion of the mammalian genomic sequence of interest, as well as functional regions necessary for episomal maintenance and selection in a bacterial host. The recombination sequence usually be at least about 20 bp in length, more usually at least about 35 bp in length, preferably at least about 50 bp in length. The sequence will usually be less than about 1 kb, more usually less than about 500 bp, and preferably less than about 100 bp. Over the length of the recombination sequence, the sequence identity with the V1 genomic sequence will usually be at least about 95%, more usually at least about 99%, and preferably 100%.

The recombination sequence may be subcloned from a suitable cDNA, EST or genomic library, or may be a chemically synthesized nucleotide having a sequence that is derived from any suitable source, e.g. published sequences, sequences derived from cloned or amplified source, etc. Methods for cloning, amplification, nucleic acid sequencing and oligonucleotide synthesis are all well-known in the art and need not be described. General references for such techniques include Sambrook et al., in *Molecular Cloning: a Laboratory Manual*, Cold Spring Harbor Laboratory Press (1989) and Ausubel, supra. As an example, a BAC library may be plated or gridded out, and transferred to a membrane for hybridization. A cDNA or EST of interest is used as a hybridization probe to determine the corresponding genomic clones. The sequence of the cDNA is may then be used to generate a V2 vector to be used in conjunction with the genomic V1 vector.

V2 will have a bacterial origin of replication that is compatible with the V1 origin, i.e. both plasmids can co-exist in a single bacterial cell. The origin will maintain the vector as a single copy in the cell. As an example, the P1 and F-Factor origins of replication are compatible, single copy origins, where V1 will have one of the origins and V2 will have the other. When the two vectors recombine with each other to form a single vector, the resultant single vector is stable and maintained at a single copy.

V2 will comprise a positive selection marker functional in bacterial cells, as previously described for V1, and a positive selection marker functional in mammalian cells. Mammalian positive selection markers include neomycin resistance in conjunction with G418 or kanamycin selection; resistance to hygromycin (hyg), to histidinol (hisD), to xanthine (GPT), to bleomycin (ble); and HPRT in conjunction with hypoxanthine selection. In addition to drug selection, other screens known in the art may also be employed, e.g. luciferase (Brasier et al. (1989) *BioTechniques* 7:1116–1122), chloramphenicol acetyltransferase (Gorman et al. (1982) *Mol. Cell. Biol.* 2:1044–1051) or β-galactosidase (An et al. (1982) *Mol. Cell. Biol.* 2:1628–1632). The V2 sequences, replication origin, and drug resistance markers are selected such that the only sequence identity of greater than 20 bp that exists between V1 and V2 is in the recombination sequence and the V1 genomic sequence of interest, i.e. the backbone sequences of the vectors are not homologous.

Optionally, V2 will also contain a bacterial negative selection marker to provide a forward selection for the desired homologous recombination event in bacterial cells (illustrated in FIG. 2B and 2C). An example of a gene useful for bacterial negative selection is the SacB gene (Pierce et al., supra.). Other negative selection markers include the CcdB gene (from pZERO, Invitrogen). In V2, the specific sequence of homology with the genomic DNA is inserted between a bacterial promoter that regulates transcription of the negative selection marker, and the coding region of the negative selection marker. The specific sequence of homology for such constructs will not contain a transcriptional termination region, and will have a length as previously defined. Upon integration of V2 into V1 and homologous recombination between the specific sequence and its cognate sequence in the genomic DNA of V1, the promoter and coding region of the negative selectable marker are separated by the entirety of V2, with the promoter located downstream of the coding region, thus preventing expression of the negative selection marker. Bacterial cells harboring V1 and V2 as two independent plasmids, which have not undergone recombination, or which harbor a recombination product between V1 and V2 but in which recombination did not occur between the specific region of homology on V2 and its cognate target sequence on V1, will continue to express the negative selection marker. Thus, under conditions which select against the expression of the negative selection marker, bacterial cells containing the desired recombination event between V1 and V2 will be highly enriched.

In order to generate the final knock-out vector construct, the V2 vector is introduced into bacterial cells carrying the V1 vector. It is preferable to transform with V2 so as to minimize the in vitro manipulation of the large genomic sequences. V2 may be introduced by any suitable method, e.g. calcium mediated transformation, electroporation, etc. The cells are selected for the presence of the two bacterial positive selection markers to isolate cells comprising both vectors.

To increase the efficiency of bacterial cell homologous transformation, RecA functionality may optionally be introduced into the transformed cells. For example, RecA can be expressed in a coordinate fashion with SacB in a synthetic operon. Upon transformation, RecA is expressed. Upon the desired recombination between V1 and V2, both SacB and RecA expression are shut down, permitting growth on sucrose and restoring the recombination deficient state of the bacterial host cell. Alternatively, RecA protein may be electroporated in trans along with V2. RecA protein is then at the highest intracellular concentrations upon electroporation and dissipates in successive divisions of the bacterial host cells. Alternatively, RecA may be expressed from a co-electroporated third vector containing a conditional origin of replication, an inducible promoter of RecA, or a conditional mutant version of RecA. In each case, RecA expression and the recombinational competence of the bacterial host cell are controlled.

When a homologous recombination event occurs, the V2 vector is inserted into V1 at the region of sequence identity with the V1 mammalian genomic sequence, thereby disrupting the genomic sequence and generating the knock-out vector. Screening for recombinant vectors may utilize the bacterial negative selection marker. Alternatively, screening may rely on the absence or presence of detectable markers, e.g. CAT, β-gal, etc., restriction analysis, Southern blotting, PCR amplification of the disrupted region, etc. After generation of a disrupted gene using the vectors and methods of the present invention, the final knock-out vector construct (e.g. FIG. 2C) is isolated from the bacterial host cells, linearized by restriction digestion at the unique site and introduced into ES cells.

For embryonic stem cells, an embryonic stem cell line may be employed or embryonic cells capable of germline transmission, e.g. zygotes, primordial germ cells, etc., may be freshly obtained from a host animal, e.g. a mouse, rat, guinea pig, chinese hamster or other small laboratory animals. The cells may be grown on an appropriate fibroblast-feeder layer or grown in the presence of leukemia inhibiting factor (LIF). Any convenient technique for introducing the DNA into the ES or embryonic cells may be employed, including calcium phosphate/DNA coprecipitates, microinjection of DNA into the nucleus, electroporation, bacterial protoplast fusion with intact cells, transfection, or the like.

After transformation of the ES cells, the cells are selected by means of positive and/or negative markers. In a preferred embodiment, which minimizes cell culture and processing, targeted ES clones are identified at the primary transformant colony level by fluorescence in situ hybridization (FISH). Alternatively strategies for identification of targeted cells as known in the art may be used. A primary colony, having from about $10^3$ to $10^5$ transformed ES cells, is picked and split into duplicate culture plates or flasks. A convenient format for further processing utilizes 96 well plates. One set of cells is maintained in culture for further expansion, while the other is processed for FISH. Exemplary protocols for FISH may be found in Trask, supra.; Ausubel et al. *Current Protocols in Molecular Biology*, John Wiley and Sons, Inc., Media PA.; and U.S. Pat. No. 5,427,910, herein incorporated by reference.

For FISH the cells are fixed in accordance with conventional techniques, and then the chromosomes are hybridized with fluorescently labeled probes prepared from all or part of the V1 genomic sequence. The DNA is labeled by any suitable technique, e.g. random priming, nick translation, PCR amplification, etc. The label may be conjugated to a primer, or the pool of nucleotides used in the reaction is labeled, so as to incorporate the label into the product. Suitable fluorochromes include fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4', 7', 4,7-hexachlorofluorescein (HEX), 5-carboxyfluorescein (5-FAM) or N, N, N', N'-tetramethyl-6-carboxyrhodamine (TAMRA), etc. The label may be a two stage system, where the amplified DNA is conjugated to biotin, haptens, etc. having a high affinity binding partner, e.g. avidin, specific antibodies, etc., where the binding partner is conjugated to a detectable label. The hybridization mix will usually include unlabeled repetitive sequences, e.g. total genomic DNA, cot1 DNA, etc. to block hybridization to repetitive elements.

Analysis of the FISH shows three regions of hybridization per genome where integration of the vector occurred randomly; two for the endogenous loci and one for the randomly integrated construct. In cells with a homologous targeting event only two regions of hybridization are seen, representing the locus at which homologous recombination has occurred and the remaining endogenous locus. The FISH screen can be completed within two days of the pick, obviating the need to feed, split, or freeze the duplicate cultures. Only clones carrying targeted events need to be expanded for frozen storage. These procedures can be optimized and adapted to scale-up automation using conventional image analyzers and robotics workstations. The homologous recombination event can be confirmed in the ES cells containing the integrated vector construct by restriction analysis, electrophoresis, Southern analysis, polymerase chain reaction or the like.

To generate transgenic animals, the targeted cells are used for embryo manipulation and blastocyst injection. Blastocysts may be obtained from 4 to 6 week old superovulated females by flushing the uterus 3.5 days after ovulation. The embryonic stem cells are then trypsinized and the modified cells added to a droplet containing the blastocysts. At least one, usually at least about 10, and up to about 30 of the modified embryonic stem cells may be injected into the blastocoel of the blastocyst. After injection, at least one and not more than about 15 of the blastocysts are returned to each uterine horn of pseudopregnant females. Females are then allowed to go to term and the resulting litters screened for cells having the construct. The blastocysts are usually chosen to have a different parentage from the transformed ES cells. By providing for a different phenotype of the blastocyst and the ES cells, chimeric progeny can be readily detected. A particularly useful phenotype is hair color, although any phenotype or genotype may be used.

The pups will usually be born 16–18 days after introduction of the blastocysts into foster mothers. The chimeric animals are screened for the presence of the knock-out at one locus (heterozygotes). Male and female heterozygotes are mated to generate homozygotes, having the knock-out at both loci. If the gene alterations cause lethality at some point in development, heterozygous strains will be maintained as breeding stock. Homozygous tissues or organs can be maintained as allogeneic or congenic grafts or transplants, or in in vitro culture. The transgenic animals may be used in functional studies, drug screening, etc.

The subject methods and transgenic animals may be used to knock-out the function of one or more genes. In the simplest form of the invention, one gene is disrupted in one genomic region. In more complex embodiments, multiple knock-outs are created. For example, the subject invention may be used to complement positional cloning techniques, which are able to localize a region of interest to a genetic interval on the order of about 50 to 1000 kb on the chromosome. Depending on the size of the genetic interval, one or more V1 vectors, encompassing the region of interest, are selected by hybridization or other mapping techniques. EST or cDNA clones that hybridize to sequences within the desired genetic interval are selected by hybridization to the genomic clones. These coding region sequences or oligonucleotides derived therefrom are subcloned into the V2 vector. In parallel reactions, or in a mixed transformation, the V2 vectors are transformed into host cells carrying the V1 vector(s). The resulting recombinant vectors comprise a series of knock-outs throughout the different genes in the genetic interval. Transgenic animals generated from these vectors are useful in determining the biological role of genes in the region.

In another embodiment of the invention, constructs are prepared that are directed to a class of genes, particularly a class sharing a sequence motif or region of high homology, e.g. SH2 domains, leucine zipper motifs, etc. An EST or cDNA library is searched by hybridization or through computer analysis for clones having the desired sequence. The selected sequences or oligonucleotides derived therefrom are subcloned into V2 vectors. Appropriate V1 vectors may be chosen through hybridization to a BAC library. The two vectors are recombined, and the resulting knock-out vectors used to generate transgenic animals. The animals are useful in determining the relative role of the class members. In addition, different knock-outs may be bred to create double mutants. It has been found that some mammalian genes are redundant, and the biological function is not revealed until all genes having the same function are disrupted.

The present invention also includes kits containing the vector systems of the present invention for the practice of the methods disclosed herein. For V1, such kits will preferably include a BAC or P1 library constructed in a suitable vector, and usually present in a bacterial host cell. For V2, the vector will usually be provided without inserts, but may have a polylinker sequence to accommodate the recombination sequence. Optionally, bacterial host cells and ES cells may also be included.

The following examples are offered by way of illustration and not by way of limitation.

EXPERIMENTAL

EXAMPLE 1

Inactivation of the Mouse Tubby Gene Using Large Scale Gene Targeting

Example 1 describes the composition and construction of pST1, a vector (V1) for insertional disruption of a genomic DNA sequence contained on another vector (V2), and the use of the modified genomic DNA sequence to disrupt the mouse tubby gene in ES cells by homologous recombination. Example 1 further describes the use of fluorescence in situ hybridization (FISH) to screen for the desired gene disruption event in ES cells and the establishment of a transgenic mouse line harboring a disruption in the tubby gene.

Construction of the recombination vector pST1: The recombination vector pST1 contains the following components: a single copy number plasmid maintenance system derived from the P1 cloning vector pSacBII (Pierce et al. (1992) *PNAS* 89:2056–2060), a PGKneo cassette, conferring G418 resistance in mammalian cells derived from pPNT (Tybulewicz et al. (1991) *Cell* 65:1153–1163), the cloning site and SacB selectable marker system from pSacBII, the RecA gene inserted downstream of the SacB gene, and a pUC19 fragment, conferring high copy number propagation and ampicillin resistance, inserted at the cloning site. The details of the construction are as follows.

Step (1): Preparation of pUC vector backbone. pUC19 (New England Biolabs, NEB) is cleaved at the EcoRI and the HindIII sites to remove the polylinker, and adapter oligos that introduce a BamHI site are phosphorylated and ligated into the EcoRI and HindIII sites to generate pUCB. The sequence of the adapters are as follows: (SEQ ID NO:1) 5'-AAT TGG ATC CTA GA-3' and (SEQ ID NO:2) 5'-AGC TTC TAG GAT CC-3'. The plasmid is transformed into *E. coli* strain DH10B (Life Technologies, Inc.), and the recombinant plasmid isolated. pUCB is linearized at the BamHI site and treated with calf intestinal phosphatase (NEB).

Step (2): Preparation of SacB gene cassette. The SacB gene cassette is obtained by PCR amplification of the desired region from pSacBII. The target sequence of the first primer (o-SB1) is derived from bp1518–bp1539 of the pSacBII sequence (Genbank accession #U09128) and incorporates the termination codon of the SacB gene at bp1533 but does not include the transcription termination region at bp1543–bp1590. A BamHI site is incorporated at the 5' end of the primer. The target sequence of the second primer (o-SB2) is derived from bp51–bp65 of pSacBII, between the SpeI site and the Shine-Dalgarno sequence at bp100. A BglII site and a XhoI site site are incorporated at the 5' end of the primer.

(SEQ ID NO:3) o-SB1: 5'-TTTGCGGATCCGTTATTAGTTGACTGTCAGCTG-3'

(SEQ ID NO:4) o-SB2: 5'-TTTGCCAGATCTCTCGAGCTAGTCAATTCGGGA-3'

The amplified SacBII gene fragment is cut with Bam HI and BglII, isolated, purified, and ligated to the BamHI cut and phosphatased pUCB prepared in Step (1) above. The SacBII fragment can ligate in one of two relative orientations to pUCB. A clone with the relative orientation resulting in the placement of the Xho I site adjacent to the destroyed EcoRI site of pUCB is chosen and designated pUSB. pUSB is then cut with XhoI and phosphatase treated.

Step (3): Addition of the RecA gene. The RecA gene cassette is obtained by PCR amplification of the desired region from the RecA$^+$ recombination competent *E. coli* strain K802 (Clontech). The target sequence of the first primer (o-RA1) is derived from bp202–bp220 of the RecA sequence (Genbank accession #'s V00328 and J01672) and incorporates the Shine-Dalgarno sequence of the RecA transcript, but does not include the RecA promoter. A SalI site is incorporated at the 5' end of the primer. The target sequence of the second primer (o-RA2) is derived from bp1311–bp1330 of RecA, downstream of the termination codon at 1297. The transcription terminator sequence from the trp operon and a XhoI site site are incorporated at the 5' end of the primer.

(SEQ ID NO:5) o-RA1: 5'-TTT CCG TCG ACT ATT CCG GTA TTA CC-3'

(SEQ ID NO:6) o-RA2: 5'-TTT GCC CTC GAG AAA AAA AAG GCT CCA AAA GGA AGC CTT TAA TGA TGC GAC CCT TGT GTA TCA-3'

The amplified RecA gene fragment is cut with SalI and XhoI, isolated, purified, and ligated to the XhoI cut and phosphatased PUSB prepared in Step (2) above. The RecA fragment can ligate in one of two relative orientations to pUSB. A clone with SacB and RecA in the same transcriptional direction is chosen and designated pUSR. pUSR is then cut with XhoI and phosphatase treated.

Step (4): Addition of the PGKneo cassette The PGKneo cassette is obtained by PCR amplification of the desired region from pPNT (Tybulewicz et al., supra.). The target sequence of the first primer (o-PN1) is derived from bp71–bp90 of the pPNT sequence. A SalI site is incorporated at the 5' end of the primer. The target sequence of the second primer (o-PN2) is derived from bp1791–bp1810 of pPNT, and a XhoI site site is incorporated at the 5' end of the primer.

(SEQ ID NO:7) o-PN1: 5'-TTT TGT CGA CCT GCA GGT CAA TTC TAC C-3'
(SEQ ID NO:8) o-PN2: 5'-TTT TCTCGAGTAGAGTCAGCTTCTGATGGA-3'

The amplified PGKneo fragment is cut with SalI and XhoI, isolated, purified, and ligated to the XhoI cut and phosphatased pUSR prepared in Step (3) above. The PGKneo fragment can ligate in one of two relative orientations to pUSR. A clone with PGKneo and RecA in the same transcriptional direction is chosen and designated pUSRN. pUSRN is then cut with XhoI and phosphatase treated.

Step (5): Addition of the β-lactamase cassette. The β-lactamase cassette is obtained by PCR amplification of the desired region from pUC19. The target sequence of the first primer (o-BL1) is derived from bp2549–bp2531 of the pUC19 sequence. A SalI site is incorporated at the 5' end of the primer. The target sequence of the second primer (o-BL2) is derived from bp1639–bp1659 of pUC19, and a XhoI site site is incorporated at the 5' end of the primer.

(SEQ ID NO:9) o-BL1: 5'-TTTTTTGTCGACTATGTATCCCTCTCATGAGAC-3'
(SEQ ID NO:10) o-BL2: 5'-TTTTTTCTCGAGAATCAGTGAGGCACCTATCTCA-3'

The amplified β-lactamase fragment is cut with SalI and XhoI, isolated, purified, and ligated to the XhoI cut and phosphatased pUSRN prepared in Step (4) above. The β-lactamase fragment can ligate in one of two relative orientations to pUSRN. A clone with β-lactamase and RecA in the same transcriptional direction is chosen and designated pUSRNA. pUSRNA is then cut with XhoI and phosphatase treated.

Step (6): Addition of the P1 replicon. The P1 replicon is obtained by isolating the 10174 bp StuI fragment from pSacBII. SalI linkers are ligated to the fragment. The fragment is then cut with SpeI. SpeI-SalI adapters with an internal XbaI cleavage site are ligated to the SpeI site and the resultant fragment cut with SalI and ligated to pUSRNA prepared in Step (5). In the desired relative orientation of the P1 replicon fragment the Xba 1 site is immediately adjacent to the pUC fragment. The resultant plasmid, pUSRNAP, is cleaved at the XbaI site and phosphatase treated.

Step (7): Addition of the E. coli promoter region: XbaI adapters (o-CPCI-1, o-CPCI-2) are prepared which contain the E. coli promoter and cI operator region derived from pSacBII (bp15911–bp15975), and a BamHI site downstream of the promoter/cI. These adapters are ligated to the pUSRNAP plasmid prepared in Step (6). The desired orientation of the XbaI adapter region has the direction of transcription from the E. coli promoter in alignment with the coding strand of SacB, with the BamHI site nearest the pUC vector fragment. The resultant plasmid, pST1, is then prepared for insertion of specific targeting oligos.

(SEQ ID NO:11) o-CPCI-1: 5'-CTAGGTTGAAGGCTCTCAAGGGCATCGGTCGAG CTTGACATTGTAGGACTATAT- TGCTCTAATAAATTTGGATCC TT-3'
(SEQ ID NO:12) o-CPCI-2: 5'-CTAGAAGGATCCAAATTTATTAGAGCAATATAG TCCTACAATGTCAAGCTCGACCGATGCCCTTGAG AGCCTTCAAC-3'

Construction and Preparation of the pST1-tub targeting plasmid: The following complementary 76 bp DNA oligos derived from the tubby gene (bp43–bp114, Genbank Accession #U54643) and carrying BamHI compatible overhangs are produced (Research Genetics):

(SEQ ID NO:13) o-tbf: 5'-GATC GAA CAG AAG CAG AAG AAG AAG CGC CAA GAG CCC TTG ATG GTA CAG GCC AAT GCA GAT GGA CGG CCC CGG AGT-3'
(SEQ ID NO:14) o-tbr: 5'-GATCACTCCGGGGCCGTCCATCTGCATTGGCCT G TACCATCAAGGGCTCTTGGCGCTTCT- TCTTCTGCT TCTGTTCGATC-3' pST1 plasmid DNA is prepared for insertion of the targeting oligos by removal of the pUC stuffer fragment by BamHI digestion and purification of the large pST1 fragment. The o-tbf and o-tbr oligos are ligated to the pST1 fragment and the ligation mixture is transformed into NS3622 cells which carry a P1 cI repressor gene on a l-imm21 prophage (Current Protocols in Human Genetics, Dracopoli et al., eds.), and plated on LB agar plates with 50 μg/ml ampicillin to generate pST1-tub. Transformant colonies are isolated, expanded and pST1-tub plasmid DNA prepared by established protocols (op. cit.).

The orientation of the oligo insert is determined by PCR using primers specific to the oligo insert and to sequences derived from the E. coli promoter region or the SacB gene region, respectively. The orientation of the oligo insert relative to the pST1 plasmid sequences will determine the direction of transcription of PGKneo relative to the tubby gene in the mouse. The Primer-Pair/Oligo combinations are shown in FIG. 3.

(SEQ ID NO:15) Primer o: 5'-CTT CTG CTG CCT CAG GTT GCT-3'
(SEQ ID NO:16) Primer 1: 5'-TCA AGG GCA TCG GTC GAG CTT-3'
(SEQ ID NO:17) Primer 2: 5'-AGC TAC TGT TCC GTC AGC GTT-3'

An isolate of pST1-tub which exhibits PCR amplification with Primer o and Primer 2 but not Primer o and Primer 1 (and therefore has the oligo region in the inverted or right-to-left transcriptional orientation) is selected. Since the expression of the SacB gene can confer a growth disadvantage even in the absence of sucrose in the culture medium, the P1 cI repressor prevents expression of SacB in NS3622 cells. Nevertheless, it is important to verify that the particular pST1 plasmid preparation does not harbor detectable levels of variants carrying defective SacB genes. The functionality of the SacB gene is tested as follows: 10 independent isolates of pST1-tub are grown up to saturation in 100 ml to 1000 ml cultures in LB+50 μg/ml ampicillin. pST1-tub plasmid DNAs are prepared from these cultures according to published methods (op. cit.) and approximately 1 ng of each plasmid DNA is transformed into host cells which do not carry the P1 cI repressor, such as the DH10B or NS3539 strain. Equal aliquots of the transformed cells are plated on LB agar+50 μg/ml ampicillin plates (LB/amp) and on LB agar+50 μg/ml ampicillin+5% sucrose plates (LB/amp/suc).

The ratio of colonies arising on LB/amp/suc to LB/amp indicates the level of "false positives" to be expected in the targeting reaction described below.

An isolate of pST1-tub exhibiting low levels of SacB function loss (ratio of colonies on LB/amp plates to colonies on LBlamplsuc plates >10$^3$) is then used to build a knockout vector construct by recombination with a BAC containing the mouse tubby genomic region.

Isolation and modification of a BAC containing mouse tubby genomic DNA. A BAC containing the mouse tubby genomic region is identified from a mouse genomic BAC library (Research Genetics) prepared from 129/sv mouse genomic DNA in the BAC vector pBeloBAC (Research Genetics) as follows: High density filters (Research Genetics) of clones in the BAC are screened by colony hybridization using $^{32}$P end-labelled o-tbf or o-tbr oligo as probe, according to recommended protocols (Research Genetics). The authenticity of the tubby genomic fragment contained on the BAC clone (the "tubby BAC") is determined by testing for the presence of adjacent tubby sequences not contained on pST1-tub by PCR using o-tbe1 (derived from tubby sequence adjacent to and not contained on o-tbf/o-tbr) and o-pST. The structure of the tubby genomic region on the BAC is further analyzed by restriction mapping or partial digest southern analysis (op. cit.).

Electrocompetent cells are prepared from the tubby BAC strain according to standard procedures (*Molecular Cloning, A Laboratory Manual*, Sambrook et al., eds.). Approximately 1 to 100 ng of pST1-tub plasmid DNA is electroporated into the electrocompetent tubby BAC strain cells. The cells are then resuspended in 1 ml of LB broth, incubated at 37° C. for 60 minutes to permit expression of the selectable markers and loss of the SacB protein in SacB⁻ cells and plated on LB/amp/suc plates containing 50 µg/ml chloramphenicol (LB/amp/cm/suc). An aliquot of the transformed cells are plated on LB/amp/cm plates as a control for SacB function. Integration of the pST1-tub plasmid into the tubby BAC by homologous recombination between the tubby BAC and pST1-tub plasmid over the region of the target oligo results in the disruption of SacB transcription, permitting the formation of colonies on LB/amp/cm/suc plates.

Independent clones arising on the LB/amp/cm/suc plates are isolated, streaked out on a fresh LB/amp/cm plate, and tested for the desired recombination event by PCR using primers derived from the pST1 plasmid region and tubby gene sequences immediately adjacent to the tubby gene sequence contained on the o-tbf and o-tbr oligos (o-SB1 and o-tbe3, respectively).

(SEQ ID NO:18) o-SB1: 5'-TGC GAT CTG CCG TTT CGA TC-3'

(SEQ ID NO:19) o-tbe3: 5'-ACC ATC GAC CAC GAC GGT GA-3'

Those clones yielding a 270 bp amplification product and therefore harboring the desired integration of the pST1-tub plasmid into the tubby BAC over the region of the o-tbf/o-tbr oligo sequence are grown up and verified for full length integrity by pulsed field gel electrophoresis. The correctly modified and full length tubby BAC clone DNA (pBACtubtar) is prepared and linearized at an appropriate single cut site contained on the BAC vector backbone, such as the LoxP, cosN, NotI or SfiI sites. The linearized DNA is then purified by CsCl banding followed by dialysis against TE.

Inactivation of the tubby gene in mouse ES cells: Embryonic stem cells are maintained and prepared for electroporation of the linearized pBACtubtar targeting construct, as described (Section F, *Manipulating the Mouse Embryo, A Laboratory Manual*, Hogan et al., eds.).

Approximately 20 µg of the pBACtubtar targeting construct is electroporated into ES cells as described (Section F, op. cit.). After 24 hours at 37° C., the ES medium is removed and fresh medium containing 200 µg/ml active G418 (Geneticin, Life Technologies, Inc.) is added. The ES cells are refed with fresh ES medium+200 µg/ml G418 every 24 hours. After approximately 10 days, colonies that have integrated the pBACtubtar DNA are evident. These colonies are picked according to established methods (Section F, op. cit.) and prepared for screening of homologous recombination at the tubby locus.

FISH based screening for homologous recombination at the tubby locus. Ninety-six G418 resistant ES cell colonies are picked using a sterile micropipette tip on a Gilson Pipetman P100 and deposited in each of 96 wells of a microtitre plate containing 50 µl of trypsin solution (0.25% trypsin, 0.04% EDTA in tris buffered saline). After approximately 5 minutes of incubation at room temperature, the colony is disrupted into individual cells by triturition. It is most convenient to pick in sets of 12 colonies, such that one row of 12 is trypsinized while another row of 12 is being picked.

After dispersal of all 96 colonies, 400 µl of ES cell medium (DMEM+15% Fetal Bovine Serum+1000 U/ml LIF) is added to neutralize the trypsin. The cells are then pelleted in the microtitre plate using a Sorvall RT7000 refrigerated centrifuge at 1000 rpm. The medium is removed by vacuum aspiration and the cells are then resuspended in 500 µl ES cell medium. Approximately 10,000 ES cells are obtained from an average colony. After resuspension, 450 µl of cells are removed and deposited into individual wells of a fresh microtitre plate containing a feeder cell layer (either mitomycin C treated primary embryo fibroblasts or STO feeders, as appropriate for the particular ES cell (*Manipulating the Mouse Embryo, A Laboratory Manual*, Hogan et al., eds.)) and placed in a 37° C. 5% CO$_2$ incubator. The ES cells are then refed every 24 hours with fresh ES cell medium. The remaining 50 µl of cells are then washed 3 times in 500 µl of Phosphate Buffered Saline (PBS) to remove excess proteins in preparation for slide preparation for fluorescence in situ hybridization (FISH) and resuspended in 20 µl of PBS.

Slide preparation: A 5 µl drop of cells from each well (containing 100–250 cells) is placed onto a clean microscope slide. Multiple drops of cells are placed on a single slide to minimize the number of slides, but each drop is kept distinct and separate from the other drops. The slide is permitted to air dry. Each drop of the slide is checked visually by phase contrast microscopy to ensure that sufficient (>50) cells are on the surface of the slide but are not overlapping.

The slides are then soaked in denaturation solution (70% deionized formamide, 2×SSC) kept at 70° C. for 2 minutes. Fresh denaturation solution is prepared for each experiment. The slides are then rinsed for 2 minutes in ice-cold 70% ethanol to stop the denaturation process, and the slides are then dehydrated in 2 minute successive incubations in 80%, 95% and 100% ethanol at room temperature. The slides are then air dried.

Probe preparation and hybridization: Purified tubby BAC DNA (1 µg) is used to prepare probe by nick translation using a standard kit (Nick Translation Kit, Boeringer Mannheim) with 1 mM digoxigenin-11-dUTP in a 100 µl reaction. The probe product size is checked by boiling a 5 µl aliquot of the reaction mix, quick cooling on ice for 2 minutes and running the DNA products out on an agarose minigel. Ideally, the majority of probe fragments will be approximately 200–300 bp in length. The probe is then pelleted by ethanol precipitation with 100 μg of mouse Cot-1 DNA as carrier. The DNA pellet is resuspended in 100 μl deionized formamide and incubated at 70° C. for 10 minutes to denature the DNA. The DNA is then placed at 37° C. for 4 to 8 hours to permit preannealing of the mouse Cot-1 DNA to the repetitive elements on the tubby BAC DNA.

After preannealing, 100 μl of master hyb mix (4×SSC, 2 mg/ml BSA, 20% dextran sulfate 500,000) is added to the probe, vortexed and spun down briefly in a microcentrifuge, and layered on top of the ES cell spots on the dried slides. The layers are covered with a cover slip and the edges of the cover slip are sealed with rubber cement to prevent dessication. The slides are then incubated for 14 to 18 hours (overnight) in a humidified chamber at 37° C.

Detection of hybridized probe: The slides are removed from the humidified chamber, the rubber cement is carefully peeled off, and the coverslip is carefully removed. The slides are washed for 15 minutes in 50% formamide/2×SSC at 39° C., and then washed for 15 minutes in 2×SSC at 39° C., and then washed for 15 minutes in 1×SSC at room temperature. The slides are then equilibrated in 4×SSC at room temperature for 5 minutes. The slides are then removed and drained of excess liquid but not permitted to dry at any point.

Digoxigenin detection solution (FITC conjugated, Boeringer Mannheim) is layered onto the slides and covered with parafilm to maintain a thin layer and prevent dessication. The slides are incubated for 45 minutes at 37° C. in a humidified chamber. If the chamber is exposed to visible light, the slides are wrapped in aluminum foil to prevent light degradation of the digoxigenin detection reagents. The slides are then soaked for 10 minutes each in 4×SSC, 4×SSC+0.1% Triton X-100, and 4×SSC. Each soak is done in foil wrapped or otherwise light impermeable vessels.

Propidium iodide staining solution (stock solution: 100 ng/ml water, working solution: 1:1000 dilution in PBS) is layered onto the slides, covered with parafilm and incubated at room temperature for 10 minutes. The slides are then rinsed in 1×SSC and blotted to remove excess moisture but not permitted to dry. DABCO mounting medium (210 mM 1,4-diazobicyclo-[2,2,2]octane in 20 mM Tris, 90% glycerol) is then layered onto the stained slides and covered with a coverslip. Excess DABCO mounting medium is squeezed out and the slide sealed with nail polish. The slides are stored at −20° C. in a slidebox with dessicant.

Visualization of the slides: The slides are examined using a fluorescence microscope with epi-illumination and a FITC filter set. Wells exhibiting interphase nuclei with three spots (one each for the endogenous mouse tubby gene and one for the randomly integrated tubby BAC) are noted. Wells exhibiting interphase nuclei with only two spots are noted as candidates for a homologous recombination event.

Confirmation of gene targeting in ES cells at the tubby locus by the pBACtubtar construct is provided by metaphase chromosome analysis using pST1 as probe. Confirmed targeted ES cells demonstrate hybridization of the pST1 probe to chromosome 7 at the tubby locus.

Targeted ES cell clones are grown up from the duplicate microtitre plate, and aliquots frozen down in liquid nitrogen storage. Targeted ES clone cells are grown up in ES culture medium, and transgenic mice are produced by blastocyst injection or by aggregation chimera, as described (op. cit.).

EXAMPLE 2

Construction of pBACtubtar in a Recombination Competent Host

Tubby BAC DNA is isolated and electroporated into a recombination competent host cell such as MC1061 (Life Technologies, Inc.). Linearized pST1-tub is electroporated into the MC1061 host cell harboring an intact tubby BAC. Selection of the desired insertion of pST1-tub into the tubby BAC by homologous recombination, isolation and purification of the resultant pBACtubtar DNA, inactivation of the mouse tubby gene in ES cells and production of transgenic mice is performed as described in Example 1.

EXAMPLE 3

Lipofection of the pBACtubtar Targeting Construct into ES Cells

Lipofection of pBACtubtar into ES cells is an alternative to electroporation of the targeting construct, and requires significantly lower amounts of DNA per experiment.

ES cells are transfected in suspension using lipid-DNA complexes containing the lipid DOGS (dioctadecylamidoglycyl, Transfectam, Promega) or similarly modified cationic lipid (Transfectamine, Life Technologies, Inc.). Linearized pBACtubtar is prepared as described in Example 1. Approximately 100 ng to 1 μg of pBACtubtar DNA is used per experiment. The lipid to DNA ratio is approximately 10:1 by weight.

Confluent cultures of AB-1 embryonic stem (ES) cells on SNL76/7 fibroblast feeder layers (McMahon and Bradley (1990) Cell 62:1073) are trypsinized to yield a single cell suspension, washed with serum containing medium, and resuspended in serum free DMEM. Approximately 9 mls of cell suspension containing $3 \times 10^6$ ES cells and about $1 \times 10^5$ feeder cells are added to each of eight 60 mm petri dishes (non tissue culture treated, Falcon). One ml of the DNA-lipid mixture was added to each dish and the dishes are incubated for 3 hours at 37° C. in a humidified 5% $CO_2$ atmosphere. Dishes are swirled gently during the incubation to minimize cell attachment. The ES cells are then diluted and plated at $1 \times 10^6$ per 100 mm dish. G418 resistant colonies are harvested 9 days later and screened for inactivation of tubby as described in Example 1. For DOGS, a lipid to DNA ratio of 10:1 to 50:1 (weight:weight) gives the highest frequency of transfection. DOGS, unlike some other cationic lipids such as DOTMA (N[1-(2,3-dioleyloxy)-propyl]-N, N, N-trimethylammonium chloride, Lipofectin, Life Technologies, Inc.) does not show ES cell toxicity at 30 μg/ml. Typically, $3 \times 10^6$ to $1 \times 10^7$ ES cells are lipofected in a volume of 1.5 to 10.0 mls with an incubation period of 3 to 4 hours.

EXAMPLE 4

Identification of the Tubby Genomic Clone by Recombination

In Example 1, a BAC containing the tubby genomic region was identified prior to the recombinational construction of pBACtubtar. In this example, the identification of the tubby genomic region BAC clone and the construction of the pBACtubtar knockout vector occurs in a single step.

A mouse genomic DNA library is obtained or prepared using a cloning vector which does not retain an ampicillin resistance selectable marker after construction, such as the BAC vector pBelo BAC or the PAC vector pCYPAC (Ioannou et al. (1994) Nature Genetics 6:84) library. The library is constructed according to published methods (Current Protocols in Human Genetics, supra.) and the library is made electrocompetent for transformation. The library is then electroporated with 1 ng to 100 ng of the pST1-tub vector and plated on LB/amp/cm/suc plates and placed at 37° C. overnight. The resultant colonies are screened by PCR for the presence of a BAC containing the tubby genomic region and having integrated pST1-tub by the desired homologous recombination event over the region of o-tbf/o-tbr. Those colonies yielding a 270 bp PCR amplification product with primers o-SB1 and o-tbe3 (sequences given in Example 1) are grown up, the recombinant BAC DNA isolated and linearized at an appropriate single cutter site contained on the BAC vector backbone such as the LoxP, cosN, NotI or SfiI sites. The linearized DNA is then purified by CsCI banding followed by dialysis against TE. The purified DNA is then used for inactivation of the mouse tubby gene in ES cells and subsequent production of transgenic mice with an inactivated tubby gene as described in Example 1.

EXAMPLE 5

Gene Targeting by Pronuclear Microinjection of Zygotes

A major limitation of current gene inactivation technology is that ES cell technology is only available for certain strains of mice, in particular the 129/sv strain. While it is possible to backcross the targeted genetic alteration into the mouse strain background of choice, in some instances this approach is impractical or impossible. For instance, it is not possible to create targeted gene inactivations in rats using mouse ES cells. In this example, an alternate route to the targeted inactivation of genes by homologous recombination is provided by microinjection of zygotes, which has been demonstrated for a number of mammals such as rats, goats, sheep, pigs and cows (Manipulating the Mouse Embryo, A Laboratory Manual, Hogan et al., eds.). The very large targeting vectors that are constructed using recombinational construction enable gene targeting in zygotes at a sufficiently high frequency to make zygote microinjection a practical approach to gene knockouts.

Linearized and purified pBACtubtar DNA is prepared as described in Example 1 except that the linearized DNA is dialyzed against low EDTA TE. 10 mM Tris pH 7.5, 0.25 mM EDTA. The DNA is quantitated by DNA fluorometry and diluted in low EDTA TE to a concentration of 1 µg/ml.

Mouse zygotes are prepared from 129/Svtac mice (Taconic Farms, Germantown N.Y.) and the DNA is microinjected into pronuclei to produce founder mice according to published protocols (Manipulating the Mouse Embryo, A Laboratory Manual, Hogan et al., eds.).

Peripheral blood lymphocytes (PBLs) are prepared by retro-orbital bleeds (op. cit.) of the founder mice and separated from erythrocytes by published protocols (Current Protocols in Immunology, eds. Coligan et al., John Wiley and Sons). The PBLs are then screened for integration of pBACtubtar at the mouse tubby locus by FISH as described in Example 1.

EXAMPLE 6

Knockout Vectors for Genes Within an Interval

Positional cloning generates an interval (often called the critical region and typically several hundred to several thousand kilobases in length) defined by flanking markers within which the desired gene or genes which are mutated in the diseased or affected state are located. Methods such as cDNA selection and exon trapping (Current Protocols in Human Genetics, Dracopoli et al., eds.) can produce short fragments of the genes which are located in the critical region. The recombinational construction method makes it possible to construct knockout vectors for all the genes or gene fragments identified by these approaches.

For each trapped exon or cDNA of interest within an interval, BACs containing the cognate genomic regions are identified by hybridization of high density BAC library filters. 75 bp oligos with BamHI compatible overhangs are derived from the DNA sequences of the trapped exons or cDNAs and ligated into the targeting vector pST1 as described in Example 1. The resultant targeting vectors are then used to construct knockout vectors by integration of the pST1-oligo plasmid into the cognate BAC by the procedure detailed in Example 1. These knockout vectors are then used to produce a set of ES cell lines each carrying a targeted disruption of the cognate gene, as detailed in Example 1. Transgenic mouse lines are produced from these ES lines and the knockout is bred to homozygosity. The heterozygous and homozygous lines of mice are then screened for phenotypes by physiological, biochemical, or histopathological examination.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombination based method for the generation of a specific disruption in a cloned mammalian genomic sequence of interest, the method comprising:

contacting in a bacterial cell, (A) a first vector, containing (i) a mammalian genomic DNA sequence of interest of at least about 25 kb in length, (ii) a cleavage site for an endonuclease that cuts once in the vector backbone, (iii) a positive selection marker for said bacterial cell, and (iv) a single copy number origin of replication functional in said bacterial cell, and (B) a second vector containing (I) a recombination sequence of from about 20 to 1000 bp and having sequence identity with a portion of said genomic DNA sequence of interest, (ii) a positive selection marker for mammalian cells, (iii) a positive selection marker for said bacterial cell, and (iv) a single copy number origin of replication functional in said bacterial cell, that is disparate and compatible with said origin of replication in said first vector and maintaining said bacterial cell under conditions that promote homologous recombination; wherein said second vector integrates into said first vector by homologous recombination between said mammalian genomic DNA sequence and said recombination sequence to provide a single recombinant vector comprising an insertion in said mammalian genomic sequence of interest, which recombinant vector is stable and maintained as a single copy in said bacterial cell.

2. A method according to claim 1, wherein said second vector further comprises a bacterial promoter operably linked to a negative selection marker for bacterial cells, and said recombination sequence in said second vector is inserted between said bacterial promoter and said negative selection marker for bacterial cells.

3. A method according to claim 1, wherein said first vector further comprises a negative selection marker for mammalian cells.

4. A method according to claim 1, wherein said bacterial cell further comprises a third vector encoding RecA.

5. A method according to claim 1, wherein said bacterial cell is an E. coli cell.

6. A method for disrupting a mammalian genomic sequence of interest, the method comprising:

contacting in a bacterial cell, (A) a first vector, containing (I) a mouse genomic DNA sequence of interest of at least about 25 kb in length, (ii) a cleavage site for an endonuclease that cuts once in the vector backbone, (iii) a positive selection marker for said bacterial cell, and (iv) a single copy number origin of replication functional in said bacterial cell, and (B) a second vector containing (I) a recombination sequence of from about 20 to 1000 bp and having sequence identity with a portion of said genomic DNA sequence of interest, (ii) a positive selection marker for mammalian cells, (iii) a positive selection marker for said bacterial cell, and (iv) a single copy number origin of replication functional in said bacterial cell, that is disparate and compatible with said origin of replication in said first vector; and maintaining said bacterial cell under conditions that promote homologous recombination; wherein said second vector integrates into said first vector by homologous recombination between said mammalian genomic DNA sequence and said recombination sequence to provide a single recombinant vector comprising an insertion in said mammalian genomic sequence of interest, which recombinant vector is stable and maintained as a single copy in said bacterial cell;

isolating said recombinant vector;

linearizing said recombinant vector by cleavage of said cleavage site; and transfecting said linearized vector into mouse embryonic stem cells comprising said mammalian genomic sequence of interest.

7. A method according to claim 6, further comprising the steps of:

hybridizing said transfected mouse embryonic stem cells with a fluorescently labeled probe prepared from said genomic sequence of interest;

wherein hybridization of said probe in two regions of said transfected mouse embryonic stem cells is indicative of homologous recombination.

8. A bacterial cell comprising:

(A) a first vector, containing (i) a mammalian genomic DNA sequence of interest of at least about 25 kb in length, (ii) a cleavage site for an endonuclease that cuts once in the vector backbone, (iii) a positive selection marker for said bacterial cell, and (iv) a single copy number origin of replication functional in said bacterial cell, and (B) a second vector containing (i) a recombination sequence of from about 20 to 1000 bp and having sequence identity with a portion of said genomic DNA sequence of interest, (ii) a positive selection marker for mammalian cells, (iii) a positive selection marker for said bacterial cell, and (iv) a single copy number origin of replication functional in said bacterial cell, that is disparate and compatible with said origin of replication in said first vector.

9. A bacterial cell according to claim 8, wherein second vector further comprises a bacterial promoter operably linked to a negative selection marker for bacterial cells and said recombination sequence in said second vector is inserted between said bacterial promoter and said negative selection marker for bacterial cells.

10. A bacterial cell according to claim 9, wherein said negative selection marker is SacB.

11. A bacterial cell according to claim 8, wherein said first vector further comprises a negative selection marker for mammalian cells.

12. A bacterial cell according to claim 8, wherein said bacterial cell further comprises a third vector encoding RecA.

13. A bacterial cell according to claim 8, wherein said bacterial cell is an *E. coli* cell.

14. A bacterial cell according to claim 8, where said first vector and said second vector single copy origins of replication functional in said bacterial cell are P1 origin and F-factor origin.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AATTGGATCC TAGA                                                           14

(2) INFORMATION FOR SEQ ID NO:2:

(i) SEQUENCE CHARACTERISTICS:
              (A) LENGTH: 14 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:2:

AGCTTCTAGG ATCC                                                           14

(2) INFORMATION FOR SEQ ID NO:3:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:3:

TTTGCGGATC CGTTATTAGT TGACTGTCAG CTG                                       33

(2) INFORMATION FOR SEQ ID NO:4:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:4:

TTTGCCAGAT CTCTCGAGCT AGTCAATTCG GGA                                       33

(2) INFORMATION FOR SEQ ID NO:5:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:5:

TTTCCGTCGA CTATTCCGGT ATTACC                                              26

(2) INFORMATION FOR SEQ ID NO:6:

(i) SEQUENCE CHARACTERISTICS:
              (A) LENGTH: 63 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:6:

```
TTTGCCCTCG AGAAAAAAAA GGCTCCAAAA GGAAGCCTTT AATGATGCGA CCCTTGTGTA      60

TCA                                                                   63
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TTTTGTCGAC CTGCAGGTCA ATTCTACC                                        28
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TTTTCTCGAG TAGAGTCAGC TTCTGATGGA                                      30
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
TTTTTTGTCG ACTATGTATC CCTCTCATGA GAC                                  33
```

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
TTTTTTCTCG AGAATCAGTG AGGCACCTAT CTCA                                 34
```

(2) INFORMATION FOR SEQ ID NO:11:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CTAGGTTGAA GGCTCTCAAG GGCATCGGTC GAGCTTGACA TTGTAGGACT ATATTGCTCT     60
```

AATAAATTTG GATCCTT                                                           77

(2) INFORMATION FOR SEQ ID NO:12:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTAGAAGGAT CCAAATTTAT TAGAGCAATA TAGTCCTACA ATGTCAAGCT CGACCGATGC            60

CCTTGAGAGC CTTCAAC                                                           77

(2) INFORMATION FOR SEQ ID NO:13:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GATCGAACAG AAGCAGAAGA AGAAGCGCCA AGAGCCCTTG ATGGTACAGG CCAATGCAGA            60

TGGACGGCCC CGGAGT                                                            76

(2) INFORMATION FOR SEQ ID NO:14:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GATCACTCCG GGGCCGTCCA TCTGCATTGG CCTGTACCAT CAAGGGCTCT TGGCGCTTCT            60

TCTTCTGCTT CTGTTCGATC                                                        80

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CTTCTGCTGC TCAGGTTGC T                                                       21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA

```
    (xi) SEQUENCE DESCRIPTION: SEQ ID NO:16:

TCAAGGGCAT CGGTCGAGCT T                                              21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGCTACTGTT CCGTCAGCGT T                                              21

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TGCGATCTGC CGTTTCGATC                                                20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ACCATCGACC ACGACGGTGA                                                20
```